United States Patent
Kishi

(10) Patent No.: US 11,008,012 B2
(45) Date of Patent: May 18, 2021

(54) DRIVING CONSCIOUSNESS ESTIMATION DEVICE

(71) Applicant: TOYOTA JIDOSHA KABUSHIKI KAISHA, Toyota (JP)

(72) Inventor: Hiroshi Kishi, Toyota (JP)

(73) Assignee: TOYOTA JIDOSHA KABUSHIKI KAISHA, Toyota (JP)

(*) Notice: Subject to any disclaimer, the term of this patent is extended or adjusted under 35 U.S.C. 154(b) by 52 days.

(21) Appl. No.: 16/456,933

(22) Filed: Jun. 28, 2019

(65) Prior Publication Data

US 2020/0047765 A1    Feb. 13, 2020

(30) Foreign Application Priority Data

Aug. 7, 2018  (JP) .............................. JP2018-148465

(51) Int. Cl.
| | | |
|---|---|---|
| *B60W 40/08* | (2012.01) | |
| *G05D 1/00* | (2006.01) | |
| *B60W 30/18* | (2012.01) | |

(52) U.S. Cl.
CPC ............ *B60W 40/08* (2013.01); *B60W 30/18* (2013.01); *G05D 1/0088* (2013.01); *B60W 2040/0818* (2013.01); *B60W 2540/26* (2013.01)

(58) Field of Classification Search
CPC ......... B60W 60/0051; B60W 60/0053; B60W 40/08; B60W 30/18; B60W 60/001;
(Continued)

(56) References Cited

U.S. PATENT DOCUMENTS

| | | | |
|---|---|---|---|
| 10,657,397 B2* | 5/2020 | Ryu ................... | G06K 9/00617 |
| 2014/0125474 A1* | 5/2014 | Gunaratne ............ | G08G 1/163 |
| | | | 340/439 |

(Continued)

FOREIGN PATENT DOCUMENTS

| | | | | |
|---|---|---|---|---|
| EP | 3438948 A1 * | 2/2019 | ............... | G08G 1/04 |
| JP | 2016034782 * | 3/2016 | ............ | B60W 30/09 |

(Continued)

OTHER PUBLICATIONS

Anna Feldhutter et al., "A New Approach for a Real-Time Non-Invasive Fatigue Assessment System for Automated Driving", The fatigue assessment system based on eyelid opening and head movement, presented at HFES International Annual Meeting in USA, Oct. 2018, 5 pages.

*Primary Examiner* — Peter D Nolan
*Assistant Examiner* — Kenneth M Dunne
(74) *Attorney, Agent, or Firm* — Sughrue Mion, PLLC

(57) ABSTRACT

A driving consciousness estimation device includes a driving readiness degree estimation unit configured to estimate a driving readiness degree relating to a driving consciousness of a driver based on a reaction time or a width of field of view of the driver and at least one of a time duration of eye glance away from road environment and an arousal level of the driver. An influence of the reaction time or the width of the field of view on the driving readiness degree estimated by the driving readiness degree estimation unit is greater than an influence of at least one of the time duration of eye glance away from road environment and the arousal level on the driving readiness degree.

9 Claims, 15 Drawing Sheets

(58) Field of Classification Search
CPC . B60W 2040/0818; B60W 2040/0872; B60W 60/0015; B60W 2540/229; G06K 9/00845; G05D 1/0088; G05D 1/0061
See application file for complete search history.

(56) References Cited

U.S. PATENT DOCUMENTS

| | | | |
|---|---|---|---|
| 2016/0001781 A1* | 1/2016 | Fung | B60K 28/02 |
| | | | 701/36 |
| 2017/0313319 A1 | 11/2017 | Kishi et al. | |
| 2019/0077409 A1* | 3/2019 | Zandi | B60W 40/08 |
| 2019/0318181 A1* | 10/2019 | Katz | A61B 5/163 |
| 2020/0189518 A1* | 6/2020 | Sawai | A61B 5/18 |

FOREIGN PATENT DOCUMENTS

| | | |
|---|---|---|
| JP | 2017-182249 A | 10/2017 |
| JP | 2017-199279 A | 11/2017 |

* cited by examiner

| REACTION TIME | AROUSAL LEVEL | INATTENTION TIME | | |
|---|---|---|---|---|
| | | LONG | MEDIUM | SHORT |
| SHORT | HIGH | Medium High | Medium High | High |
| | LOW | Medium | Medium High | Medium High |

| REACTION TIME | AROUSAL LEVEL | INATTENTION TIME | | |
|---|---|---|---|---|
| | | LONG | MEDIUM | SHORT |
| LONG | HIGH | Low | Low | Medium Low |
| | LOW | × (N/A) | Low | Low |

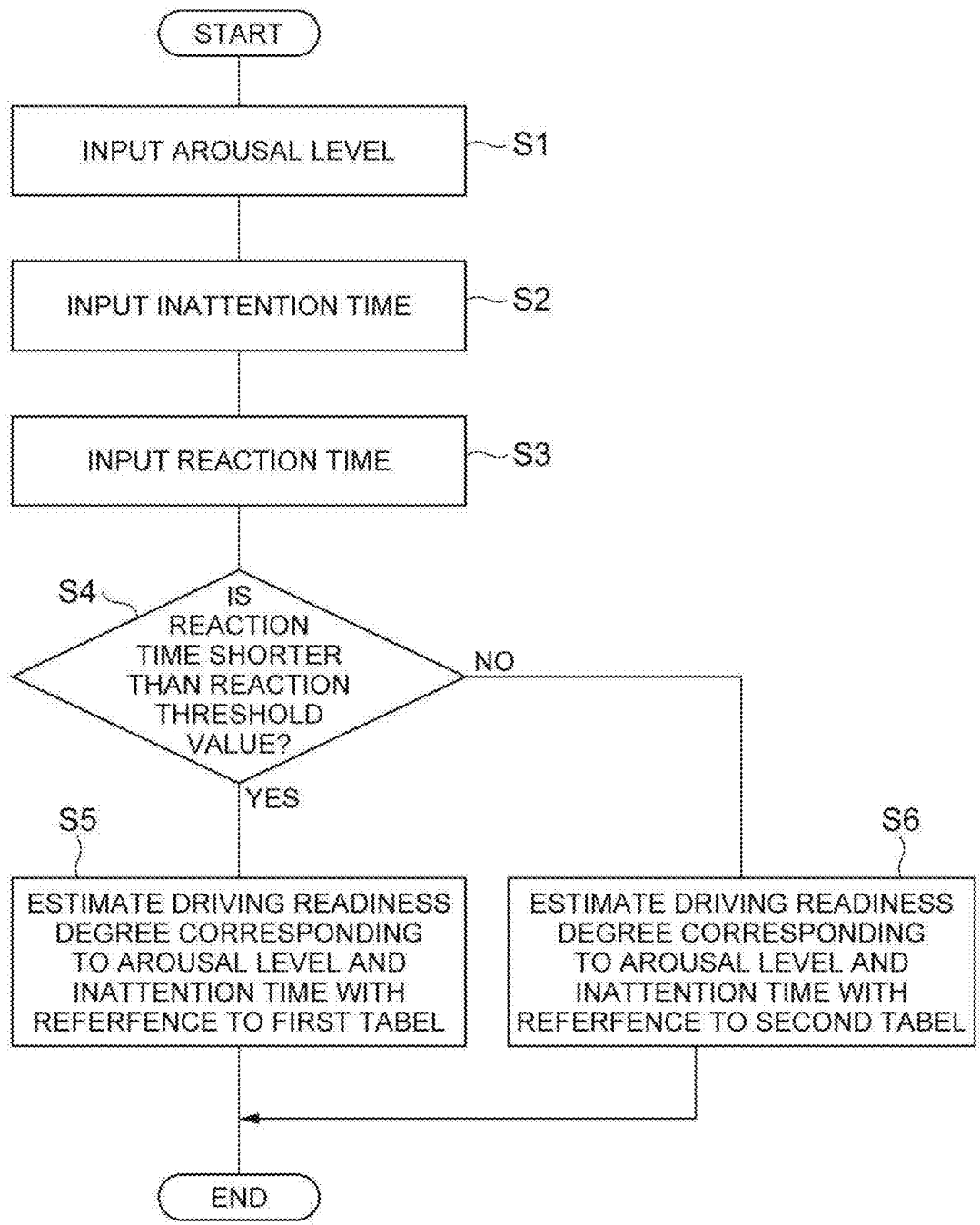

Fig.4

| TASK DEMAND ESTIMATION FACTOR | | DETERMINATION OF TASK DEMAND |
|---|---|---|
| (a) FOLLOW-UP TRAVELING | (b) TRAVELING ON CURVE | |
| PRECEDING INTER-VEHICLE TIME IS EQUAL TO OR LONGER THAN 1.0 SECOND | LATERAL ACCELERATION IS EXPECTED TO BE LOWER THAN 2 m/s² | DETERMINE TASK DEMAND AS "LOW" IF BOTH TASK DEMAND ESTIMATION FACTORS (a) AND (b) ARE APPLICABLE |
| | | DETERMINE TASK DEMAND AS "HIGH" IF BOTH TASK DEMAND ESTIMATION FACTORS (a) AND (b) ARE NOT APPLICABLE |

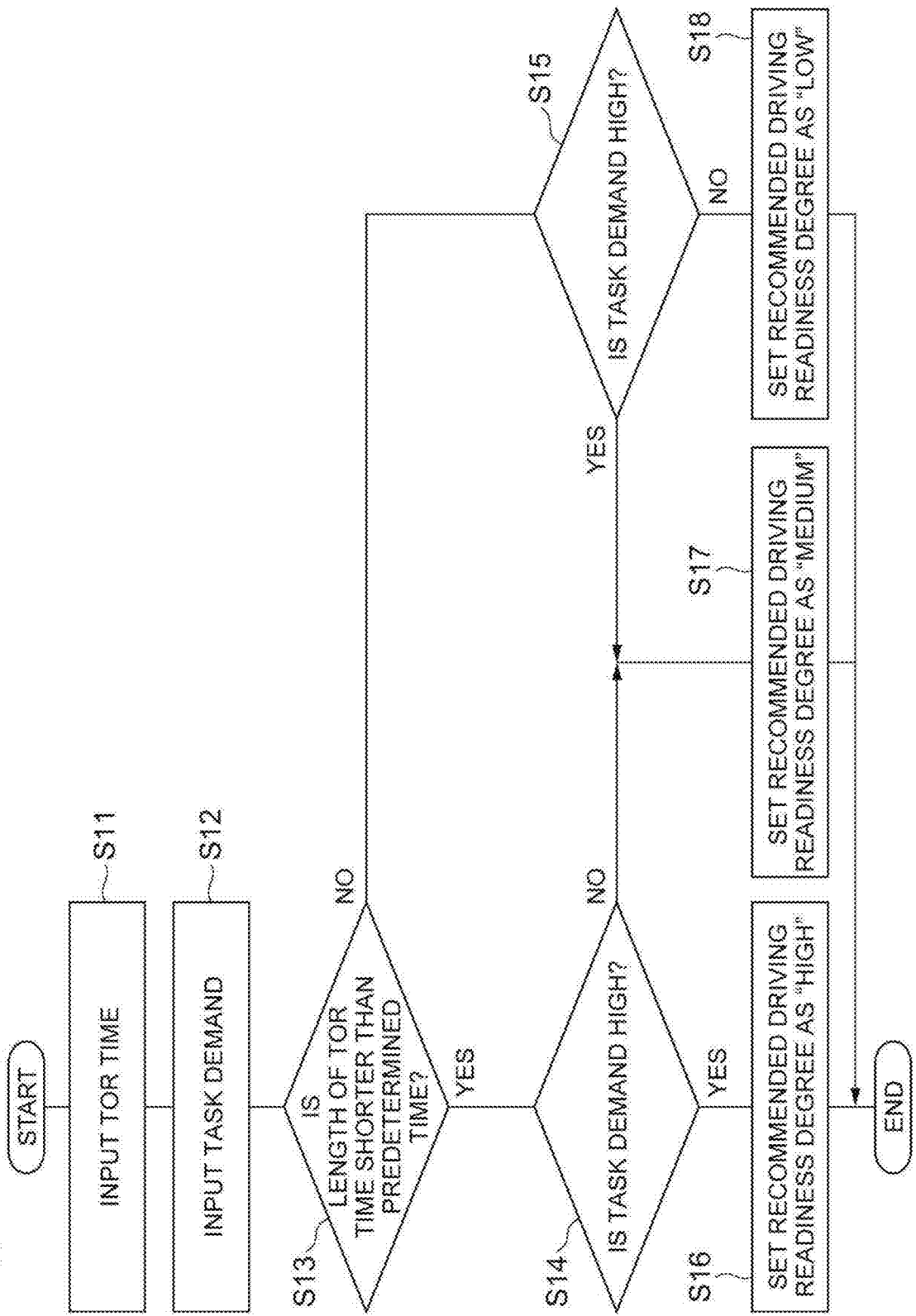

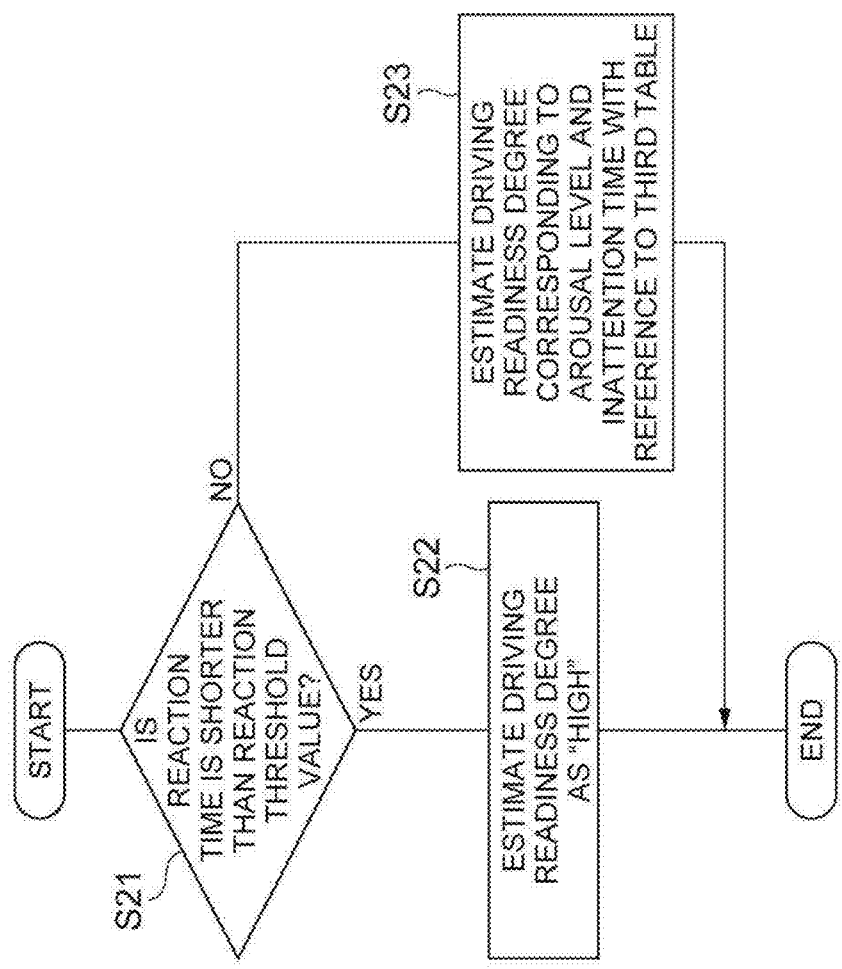

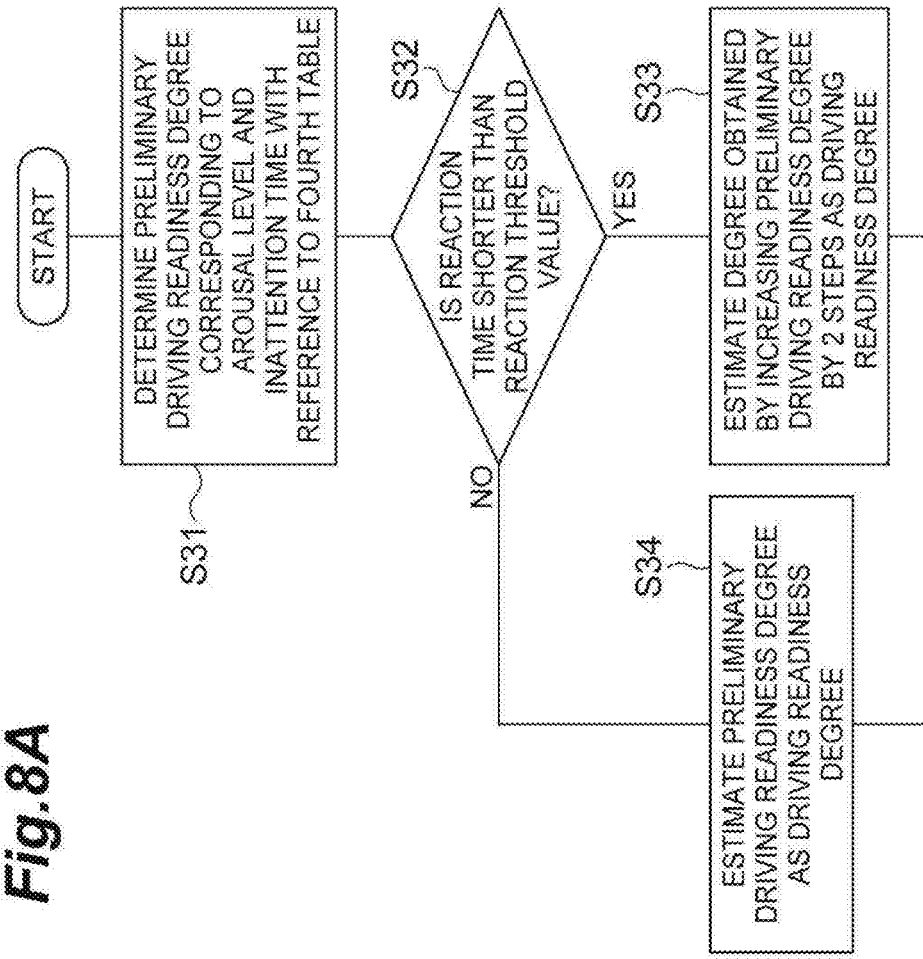

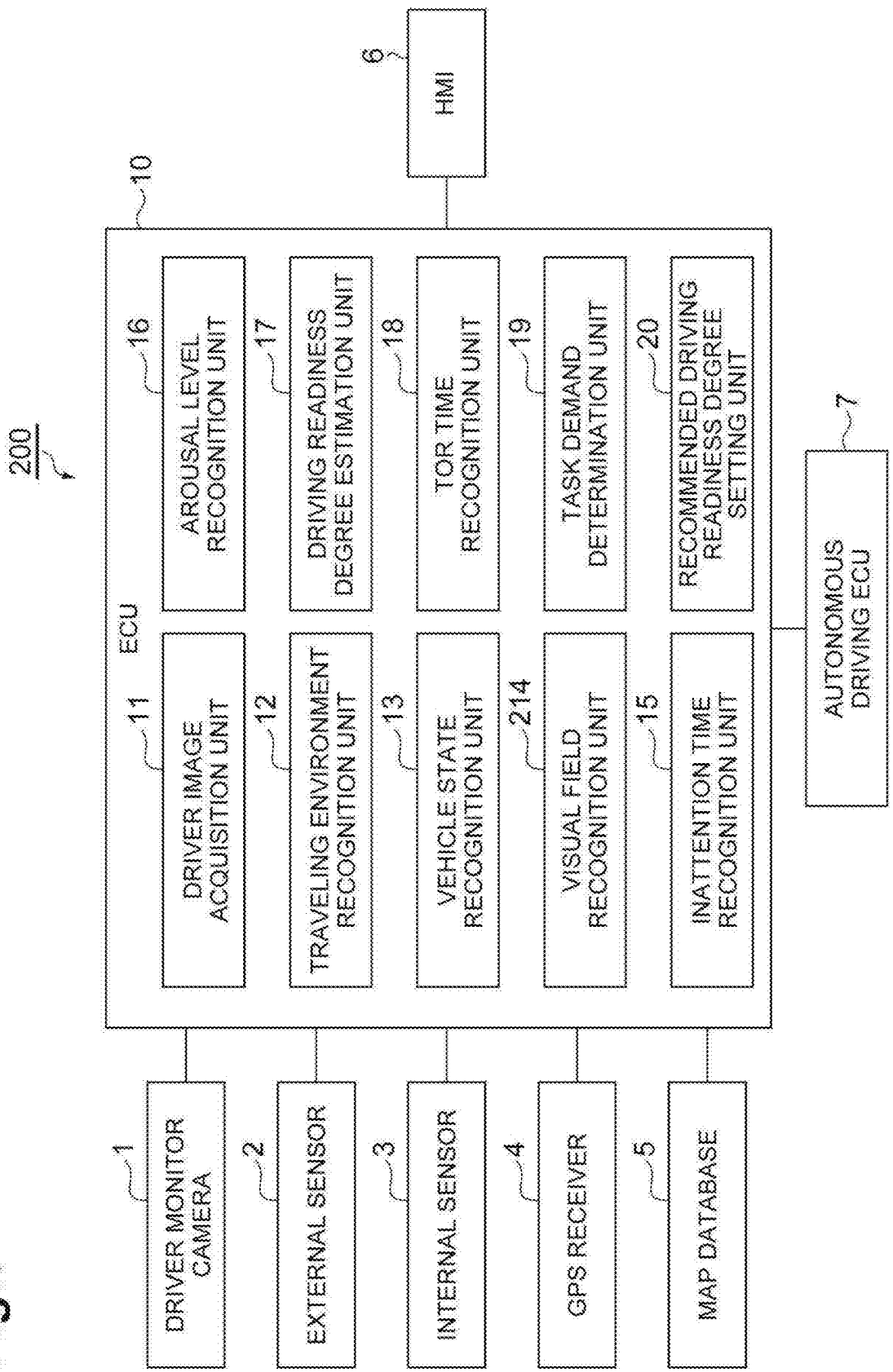

| WIDTH OF FIELD OF VIEW | AROUSAL LEVEL | INATTENTION TIME | | |
|---|---|---|---|---|
| | | LONG | MEDIUM | SHORT |
| WIDE | HIGH | Medium High | Medium High | High |
| | LOW | Medium | Medium High | Medium High |

| WIDTH OF FIELD OF VIEW | AROUSAL LEVEL | INATTENTION TIME | | |
|---|---|---|---|---|
| | | LONG | MEDIUM | SHORT |
| NARROW | HIGH | Low | Low | Medium Low |
| | LOW | ×(N/A) | Low | Low |

DRIVING CONSCIOUSNESS ESTIMATION DEVICE

TECHNICAL FIELD

An aspect of the present disclosure relates to a driving consciousness estimation device.

BACKGROUND

A device disclosed in Japanese Unexamined Patent Publication No. 2017-199279 is known as a technology relating to a driving consciousness estimation device. In the driving consciousness estimation device disclosed in Japanese Unexamined Patent Publication NO. 2017-199279, a driving readiness degree relating to a driving consciousness of a driver is estimated based on a driver image of the vehicle driver and a traveling environment around a vehicle. A traveling environment requirement degree, which is an index to the driving readiness degree required for the driver, is estimated based on the traveling environment. A warning is performed on the driver based on a result of comparison between the driving readiness degree and the traveling environment requirement degree.

SUMMARY

In the driving consciousness estimation device described above, the driving readiness degree is estimated from a reaction of the driver, however, an arousal level or the like of the driver can be used as a factor required for estimating the driving readiness degree in addition to the reaction of the driver. In this case, it is desirable to provide a driving consciousness estimation device that can improve a driving safety while further taking the driving safety into consideration in estimating the driving readiness degree.

An aspect of the present disclosure is to provide a driving consciousness estimation device that can improve the driving safety.

A driving consciousness estimation device according to an aspect of the present disclosure includes a driving readiness degree estimation unit configured to estimate a driving readiness degree relating to a driving consciousness of a driver based on a reaction time or a width of field of view of the driver of a vehicle and at least one of a time duration of eye glance away from road environment and an arousal level of the driver. An influence of the reaction time or the width of the field of view on the driving readiness degree estimated by the driving readiness degree estimation unit is greater than an influence of at least one of the time duration of eye glance away from road environment and the arousal level on the driving readiness degree.

It can be seen that the reaction time or the width of the field of view of the driver further contributes to the driving safety than the time duration of eye glance away from road environment and the arousal level of the driver. Therefore, in the driving consciousness estimation device according to the aspect of the present disclosure, the influence of the reaction time or the width of the field of view on the driving readiness degree is set greater than the influence of at least one of the time duration of eye glance away from road environment and the arousal level. As a result, it is possible to estimate the driving readiness degree with sufficient consideration of the driving safety, and thus, it is possible to improve the driving safety.

In the driving consciousness estimation device according to an aspect of the present disclosure, the driving readiness degree estimation unit may be configured to estimate the driving readiness degree based on the width of the field of view and at least one of the time duration of eye glance away from road environment and the arousal level, if the driver is driving the vehicle with manual driving. At the time of manual driving in which it is difficult to appropriately determine the reaction of the driver, it is possible to appropriately estimate the driving readiness degree based on the width of the field of view of the driver.

According to an aspect of the present disclosure, it is possible to provide a driving consciousness estimation device that can improve the driving safety.

BRIEF DESCRIPTION OF THE DRAWINGS

FIG. 2A is a diagram illustrating a first table.

FIG. 2B is a diagram illustrating a second table.

FIG. 3 is a flowchart illustrating an example of processing for estimating a driving readiness degree.

FIG. 4 is a table explaining an example of determining a task demand.

FIG. 5 is a flowchart illustrating processing for setting a recommended driving readiness degree.

FIG. 7A is a flowchart illustrating another example of processing for estimating the driving readiness degree.

FIG. 7B is a diagram illustrating a third table.

FIG. 8A is a flowchart illustrating still another example of processing for estimating the driving readiness degree.

FIG. 8B is a diagram illustrating a fourth table.

FIG. 9 is a block diagram illustrating a driving consciousness estimation device according to a second embodiment.

FIG. 12A is a diagram illustrating a fifth table.

FIG. 12B is a diagram illustrating a sixth table.

DETAILED DESCRIPTION

Figure 1:
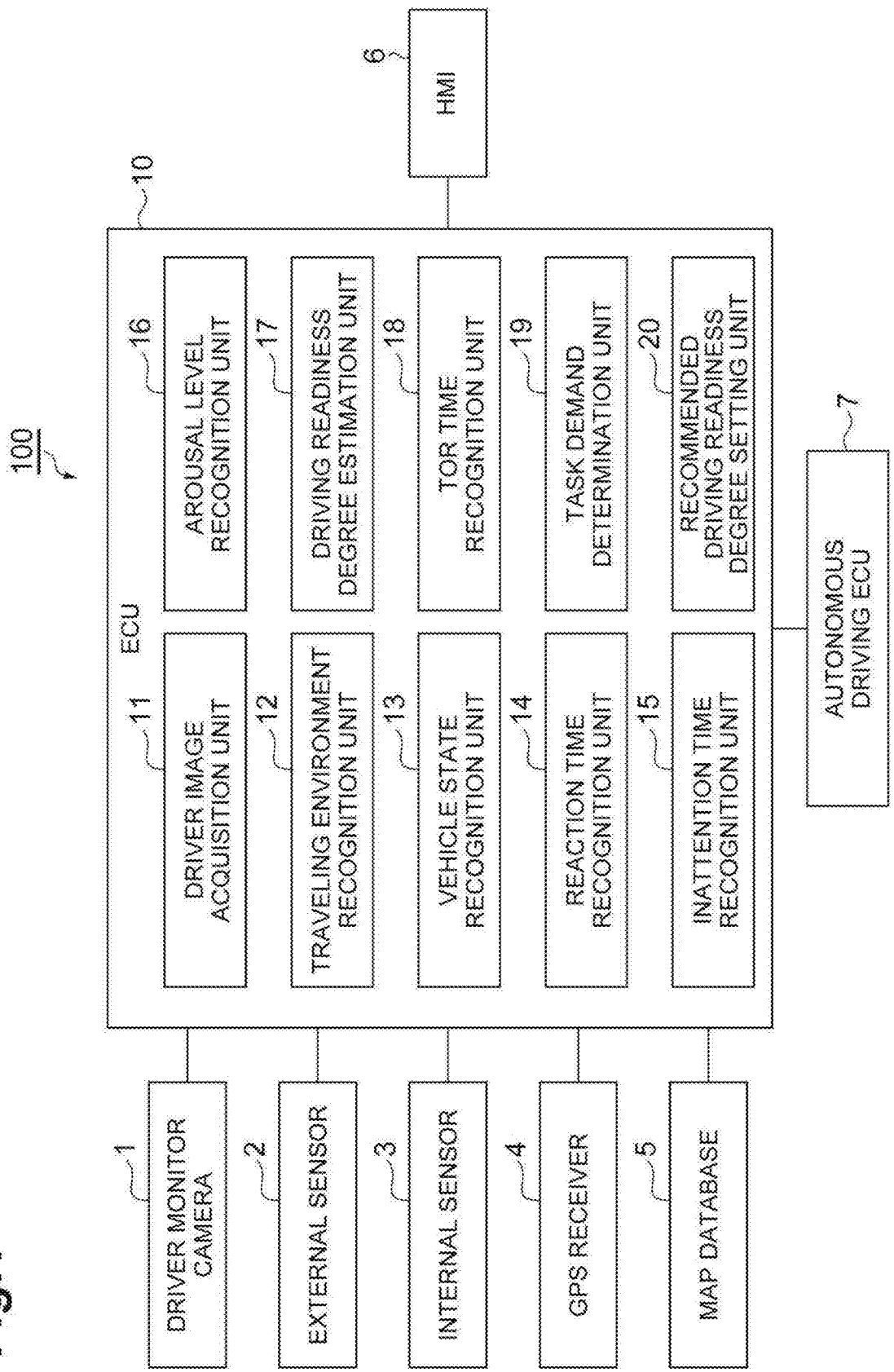
FIG. 1 is a block diagram illustrating a driving consciousness estimation device according to a first embodiment.

Hereinafter, embodiments of the present disclosure will be described with reference to the drawings. In the description below, the same reference numerals are used for the same or equivalent elements, and redundant explanations will not be repeated.

First Embodiment

As illustrated in FIG. 1, a driving consciousness estimation device 100 in a first embodiment is a device that performs an estimation of a driving readiness degree relating to a driving consciousness of a driver of a host vehicle (vehicle) (hereinafter, simply referred to as a driver). The driving readiness degree will be described later. The driving consciousness estimation device 100 may form a part of an autonomous driving system that performs autonomous driving of the host vehicle.

The driving consciousness estimation device 100 includes an electronic control unit (ECU) 10 that generally manages the device. The ECU 10 is an electronic control unit including a central processing unit (CPU), read only memory (ROM), random access memory (RAM) and the like. In the ECU 10, various functions are realized by a program stored in the ROM being loaded on the RAM and the CPU executing the program loaded on the RAM. The ECU 10 may be configured to include a plurality of electronic control units.

A driver monitor camera 1, an external sensor 2, an internal sensor 3, a global positioning system (GPS) receiver 4, a map database 5, and an HMI 6 are connected to the ECU 10. The ECU 10 is connected to an autonomous drive ECU 7.

The driver monitor camera 1 is provided on a cover of a steering column of the host vehicle and in front of the driver, and images a head of the driver. Since the driver monitor camera 1 images the driver from plural directions, plural number of cameras may be provided. The driver monitor camera 1 transmits a driver image in which the driver is imaged to the ECU 10.

The external sensor 2 is a detection device that detects a surrounding environment of the host vehicle. The external sensor 2 includes a camera and a radar sensor. The camera is provided, for example, on the inner side of windshield of the host vehicle and images the front of the host vehicle. The camera may be provided on the rear surface or the side surface of the host vehicle. The camera transmits image information relating to surroundings of the host vehicle to the ECU 10. The camera may be a monocular camera or may be a stereo camera. The stereo camera has two imaging units that are arranged so as to reproduce a binocular parallax.

The radar sensor is a detection device that detects obstacles around the host vehicle using radio waves (for example, millimeter waves) or light. The radar sensor includes, for example, millimeter wave radar or a light detection and ranging (LIDAR). The radar sensor transmits the radio wave or light to the surroundings of the host vehicle, and detects the obstacles by receiving radio waves or light reflected from obstacles. The radar sensor transmits the detected obstacle information to the ECU 10. Obstacles include fixed objects such as guardrails and buildings, and pedestrians, bicycles, other vehicles, and the like.

The internal sensor 3 is a detection device that detects a vehicle state of the host vehicle. The internal sensor 3 includes a vehicle speed sensor, an accelerator sensor, and a yaw rate sensor. The vehicle speed sensor is a measuring device that measures a speed of the host vehicle. As the vehicle speed sensor, for example, a vehicle wheel speed sensor is used, which is provided on vehicle wheels of the host vehicle or on a drive shaft rotating integrally with vehicle wheels, and measures a rotational speed of the vehicle wheels. The vehicle speed sensor transmits the measured vehicle speed information (vehicle wheel speed information) to the ECU 10.

The accelerator sensor is a measuring device that measures an acceleration of the host vehicle. The accelerator sensor includes, for example, a longitudinal accelerator sensor that measures acceleration in the longitudinal direction of the host vehicle and a lateral accelerator sensor that measures a lateral acceleration of the host vehicle. The accelerator sensor transmits, for example, acceleration information of the host vehicle to the ECU 10. The yaw rate sensor is a measuring device that measures a yaw rate (rotation angular velocity) around the vertical axis at the center of gravity of the host vehicle. As the yaw rate sensor, for example, a Gyro sensor can be used. The yaw rate sensor transmits the measured yaw rate information of the host vehicle to the ECU 10.

The GPS receiver 4 measures the position of the host vehicle (for example, the latitude and longitude of the host vehicle) by receiving a signal from three or more GPS satellites. The GPS receiver 4 transmits the measured position information on the host vehicle to the ECU 10. The driving consciousness estimation device 100 may acquire the position information on the host vehicle using a simultaneous localization and mapping (SLAM) technology which uses the result of detection performed by the external sensor 2 and map information, instead of the GPS.

The map database 5 is a database storing the map information. The map database 5 is formed, for example, in a hard disk drive (HDD) mounted on the host vehicle. The map information includes information on the position of the road, information on the shape of the road (for example, types of curves or straight roads, a curvature of the curve, or the like), information on the width of the road, information on the height of the road, information on the location of the intersection, merging point, and the branch, and information on the position of a building. The map information may include position information relating to an installed object on the road such as a guide plate, a sign, or the like. The map database 5 may be stored in a computer in a facility such as a management center that can communicate with the host vehicle.

The HMI 6 is an interface that performs inputting and outputting of the information between the driving consciousness estimation device 100 and the driver. The HMI 6 includes, for example, a display unit (display) and a speaker of the host vehicle. The HMI 6 outputs an image on the display and outputs a voice from the speaker according to a control signal from the ECU 10. The HMI 6 may include a head up display (HUD).

The autonomous drive ECU 7 is an electronic control unit that is mounted on the host vehicle and executes an autonomous driving of the host vehicle. The autonomous driving means a vehicle control causing the host vehicle to travel autonomously without the driving operation by the driver. In the Society of Automotive Engineers (SAE) J3016, autonomous driving level 0 to autonomous driving level 4 are defined according to the degree of the autonomous driving. The autonomous drive ECU 7 generates a travel plan along a preset target route based on the position information of the host vehicle from the GPS receiver 4, the map information in the map database 5, and a traveling environment and the vehicle state of the host vehicle described below. The target route here is set by a navigation system. The autonomous drive ECU 7 executes the autonomous driving according to the travel plan. The autonomous drive ECU 7 executes the autonomous driving by transmitting the control signal to an actuator (an engine actuator, a steering actuator, a brake actuator, or the like) of the host vehicle. The autonomous drive ECU 7 generates the travel plan using a known method and executes the autonomous driving. The autonomous drive ECU 7 may perform a travel control to make the vehicle follow the preceding vehicle and cause the host vehicle to autonomously drive so as to follow the preceding vehicle.

During the execution of the autonomous driving, for example, when the override operation is performed, the autonomous drive ECU 7 releases the execution of autonomous driving and shifts a driving mode to a manual driving (that is, switches the driving of the host vehicle to the manual driving from the autonomous driving. The override operation is an intervention operation by the driver for shifting the driving mode of the host vehicle from the autonomous driving to the manual driving. The autonomous drive ECU 7 shifts the driving mode to the manual driving by gradually decreasing a control command value to the actuator of the host vehicle down to zero. The manual driving also includes a case where a well-known driving support control that supports the driving operation is executed.

Next, a functional configuration of the ECU 10 will be described. A part of the functions of the ECU 10 described below may be an aspect of being executed by the computer in the facility such as the management center that can communicate with the host vehicle and/or by the autonomous drive ECU 7. The ECU 10 may be integrated with the autonomous drive ECU 7.

The ECU 10 includes a driver image acquisition unit 11, a traveling environment recognition unit 12, a vehicle state recognition unit 13, a reaction time recognition unit 14, an inattention time (a time duration of eye glance away from road environment) recognition unit 15, an arousal level recognition unit 16, a driving readiness degree estimation unit 17, a take over time (TOR) recognition unit 18, a task demand determination unit 19, and a recommended driving readiness degree setting unit 20.

The driver image acquisition unit 11 acquires a driver image from the driver monitor camera 1. If the driver monitor camera 1 includes plural cameras, the driver image acquisition unit 11 acquires the driver images from each camera in association with each other.

The traveling environment recognition unit 12 recognizes the traveling environment around the host, vehicle. The traveling environment recognition unit 12 recognizes the traveling environment based on the result of detection by the external sensor 2, the position information from the GPS receiver 4, the map information in the map database 5 and the information relating to the autonomous driving from the autonomous drive ECU 7. The traveling environment recognition unit 12 recognizes the traveling environment around the host vehicle using a known method. A situation of obstacles around the host vehicle and a road situation are included in the traveling environment. The traveling environment recognition unit 12 does not necessarily need to use the information of the autonomous drive ECU 7 and may only use the result of detection performed by the external sensor 2.

The traveling environment recognition unit 12 recognizes the situation of the obstacles around the host vehicle based on the result of detection performed by the external sensor 2. Positions of the obstacle with respect to the host vehicle, a relative speed of the obstacle with respect to the host vehicle, a moving direction of the obstacle with respect to the host vehicle, and the like are included in the situations of the obstacles around the host vehicle. The traveling environment recognition unit 12 may recognize lane lines based on captured images in front of the host vehicle by the camera of external sensor 2 using a well-known method. The traveling environment recognition unit 12 can recognize the interruption vehicle which interrupts in front of the host vehicle, a braking preceding vehicle, an overtaking vehicle that overtakes the host vehicle from the side, or the like using a well-known method.

The traveling environment recognition unit 12 recognizes road shapes (curves, intersections, merging sections, and the like) in front of the host vehicle as road conditions based on the result of detection performed by the external sensor 2. The traveling environment recognition unit 12 may recognize the number of vehicles traveling on each road shape using a well-known method. The traveling environment recognition unit 12 may recognize the road shape in front of the host vehicle from the position information and the map information on the host vehicle or may recognize the installed object on the road from the position information and map information on the host vehicle.

The vehicle state recognition unit 13 recognizes a state of the host vehicle during traveling based on the result of detection performed by the internal sensor 3. The vehicle state includes the vehicle speed of the host vehicle, the acceleration of the host vehicle, and the yaw rate of the host vehicle. Specifically, the vehicle state recognition unit 13 recognizes the vehicle speed of the host vehicle based on the vehicle speed information from the vehicle speed sensor. The vehicle state recognition unit 13 recognizes the acceleration of the host vehicle (the longitudinal acceleration and the lateral acceleration) based on the acceleration information from the accelerator sensor. The vehicle state recognition unit 13 recognizes the yaw rate of the host vehicle based on the yaw rate information from the yaw rate sensor.

The reaction time recognition unit 14 recognizes a reaction time (a reaction delay) of the driver. The reaction time includes a peripheral reaction time and a vehicle behavior reaction time. The reaction time recognition unit 14 recognizes the reaction time from the timing when the viewing target is seen by the driver to the timing when the driver visually recognizes the viewing target as the peripheral vision reaction time. The reaction time recognition unit 14 recognizes the reaction time from the timing when the viewing target is seen by the driver to the timing when the driver executes the vehicle behavior against the viewing target as the vehicle behavior reaction time. The method of recognizing the reaction time is not particularly limited, and various well-known methods can be adopted.

The viewing target can be detected from the traveling environment recognized by the traveling environment recognition unit 12. The viewing target includes at least one of a surrounding vehicle, a road shape, and an installed object on the road. A line of sight of the driver can be detected from the driver image acquired by the driver image acquisition unit 11. The line of sight of the driver can be detected by detecting eyeballs and movements of the eyeballs of the driver from the driver image using a well-known method. The vehicle behavior can be detected from the state of the host vehicle recognized by the vehicle state recognition unit 13.

The inattention time recognition unit 15 recognizes a time duration of eye glance away from road environment (inattention time) which is a time the inattention of the driver continues based on the driver image acquired by the driver image acquisition unit 11, for example. The method of recognizing the inattention time is not particularly limited, and various well-known methods can be adopted.

The arousal level recognition unit 16 recognizes the arousal level of the driver from the eye closing rate of the driver per minute, an eye open situation, a blinking frequency, or the movement of eyeballs, and the like, based on the driver image acquired by the driver image acquisition unit 11. The arousal level recognition unit 16 may recognize the arousal level of the driver based on the state of the host vehicle recognized by the vehicle state recognition unit 13. The arousal level is a degree indicating that the consciousness of the driver is not in a state of being hazy due to lack of sleep or the like, but in an awakening state. The method of recognizing the arousal level is not particularly limited, and various well-known methods can be adopted.

The driving readiness degree estimation unit 17 estimates the driving readiness degree based on the reaction time recognized by the reaction time recognition unit 14, the inattention time recognized by the inattention time recognition unit 15, and the arousal level recognized by the arousal level recognition unit 16. The driving readiness degree is a degree according to the height of the driving consciousness of the driver. The driving consciousness is a generic term for mental activities including cognition, prediction, determination, and an operation when the driver drives a vehicle.

The driving readiness degree is a level of readiness for the driving by the driver. The driving readiness degree is also called "readiness". As the driving consciousness and the degree of readiness of the driver against the traveling environment of the host vehicle increase, the value of driving readiness degree increases. As an example, the driving readiness degree here can be divided into five stages such as Low (low), Medium Low (slightly low), Medium (normal), Medium High (slightly high) and High (high). The way of expressing the driving readiness degree is not particularly limited, and may be expressed by a numerical value or may be divided into plural stages.

The driving readiness degree estimation unit 17 estimates the driving readiness degree referring to a first table T1 (refer to FIG. 2A) and a second table T2 (refer to FIG. 2B). The first table T1 is a table when the reaction time is shorter than a reaction threshold value (threshold value) set in advance. The second table 12 is a table when the reaction time is equal to or longer than the reaction threshold value. The first table T1 and the second table T2 are determined in advance, and are stored in a storage unit (ROM or RAM) of the ECU 10, for example.

For the driving readiness degree in the first table T1 and the second table T2, the arousal level is set as "High" when the arousal level is higher than the arousal level threshold value set in advance, and is set as "Low" when the arousal level is lower than the arousal level threshold value. For the driving readiness degree in the first table T1 and the second table T2, the inattention time is set as "Long" when the inattention time is longer than a first inattention threshold value set in advance, and is set as "Short" when the inattention time is equal to or shorter than a second inattention threshold value (<first inattention threshold value), and is set as "Medium" when the inattention time is equal to or shorter than the first inattention threshold value and longer than the second inattention threshold value. In the second table 12, the driving readiness degree when the arousal level is "Low" and the inattention time is "Long" is indicated as "X (N/A)" because the driving readiness degree is extremely low and there is no corresponding degree.

As illustrated in FIG. 3, the arousal level recognized by the arousal level recognition unit 16 is input to the driving readiness degree estimation unit 17 (STEP S1). The inattention time recognized by the inattention time recognition unit 15 is input to the driving readiness degree estimation unit 17 (STEP S2). The reaction time recognized by the reaction time recognition unit 14 is input to the driving readiness degree estimation unit 17 (STEP S3).

The driving readiness degree estimation unit 17 determines whether or not the reaction time is shorter than the reaction threshold value (STEP S4). If YES in STEP S4 described above, referring to the first table T1, a first degree corresponding to the inattention time and the arousal level is estimated as the driving readiness degree (STEP S5). If NO in STEP S4 described above, referring to the second table T2, a second degree corresponding to the inattention time and arousal level is estimated as the driving readiness degree (STEP S6).

As indicated in the first table T1 and the second table T2, even if the inattention time and the arousal level change, when the reaction time is shorter than the threshold value (reaction is fast), the driving readiness degree is equal to or higher than "Medium", and when the reaction time is equal to or longer than the threshold value (reaction is slow), the driving readiness degree is lower than "Medium". If the inattention time changes by one step, the driving readiness degree does not change or changes by one step at the same arousal level and at the same reaction time. If the arousal level changes, the driving readiness degree does not change or changes by one step at the same inattention time and at the same reaction time. On the other hand, if the reaction time changes (comparing the first table T1 and the second table T2), the driving readiness degree is changed by equal to or more than two steps at the same inattention time and at the same arousal level. That is, the influence (contribution degree) of the reaction time to the driving readiness degree estimated by the driving readiness degree estimation unit 17 is greater than the influence (contribution degree) of at least one of the inattention time and the arousal level to the driving readiness degree.

The TOR time recognition unit 18 recognizes a TOR time, which is a time required for switching the driving mode of the host vehicle from the autonomous driving to the manual driving. The TOR time is a fixed value set in advance. The TOR time is stored in the storage unit of the ECU 10, for example. The TOR time may be a variable value that varies according to the vehicle state of the host vehicle.

The task demand determination unit 19 determines whether a task demand is high or low. The task demand is an ability required after the driving mode of the host vehicle is switched from the autonomous driving to the manual driving. The task demand determination unit 19 determines the task demand based on the traveling environment recognized by the traveling environment recognition unit 12 and the state of the host vehicle recognized by the vehicle state recognition unit 13.

FIG. 4 is a table explaining an example of determining the task demand. As illustrated in FIG. 4, the task demand determination unit 19 sets a fact that a follow-up traveling in which the host vehicle performs a follow-up traveling against the preceding vehicle and a preceding inter-vehicle time which is an inter-vehicle time with the preceding vehicle is equal to or longer than 1.0 second, as a task demand estimation factor (a). The task demand determination unit 19 sets a fact that the host vehicle is traveling on a curve and the lateral acceleration is expected to be lower than 2 m/s$^2$, as a task demand estimation factor (b). The task demand determination unit 19 determines the task demand as "low" if both the task demand estimation factors (a) and (b) are applicable. The task demand determination unit 19 determines the task demand as "high" if both the task demand estimation factors (a) and (b) are not applicable.

The recommended driving readiness degree setting unit 20 sets a recommended driving readiness degree which is a recommended driving readiness degree based on the TOR time recognized by the TOR time recognition unit 18 and the task demand determined by the task demand determination unit 19.

As illustrated in FIG. 5, the TOR time recognized by the TOR time recognition unit 18 is input to the recommended driving readiness degree setting unit 20 (STEP S11). The task demand determined by the task demand determination unit 19 is input to the recommended driving readiness degree setting unit 20 (STEP S12). The recommended driving readiness degree setting unit 20 determines whether or not the length of the TOR time is shorter than a predetermined time (STEP S13). This predetermined time is determined in advance, and is stored in the storage unit of the ECU 10, for example.

If YES in STEP S13 described above, the recommended driving readiness degree setting unit 20 determines whether or not the task demand is high (STEP S14). If NO in STEP S13 described above, the recommended driving readiness degree setting unit 20 determines whether or not the task demand is high (STEP S15). If YES in STEP S14 described above, the recommended driving readiness degree setting unit 20 sets the recommended driving readiness degree as "High" (STEP S16). If NO in STEP S14 or if YES in STEP S15 described above, the recommended driving readiness degree setting unit 20 sets the recommended driving readiness degree as "Medium" (STEP S17). If NO in STEP S15 described above, the recommended driving readiness degree setting unit 20 sets the recommended driving readiness degree as "Low" (STEP S18).

FIG. 6A to FIG. 6D are diagrams illustrating examples of the images displayed on the display unit 6a of the HMI 6. A trapezoidal icon indicates the state of the recommended driving readiness degree set by the recommended driving readiness degree setting unit 20. A triangular icon included in the trapezoid indicates the state of the driving readiness degree estimated by the driving readiness degree estimation unit 17.

Figure 6A:
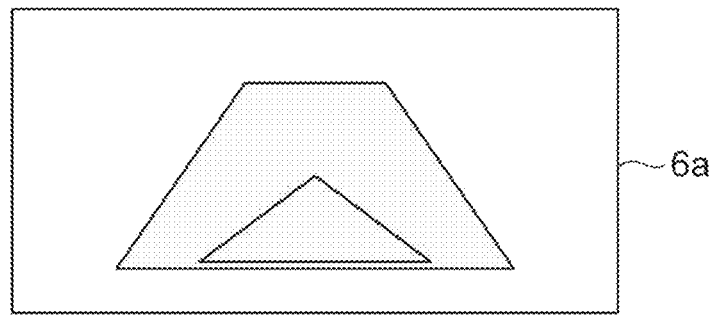
FIG. 6A is a diagram illustrating a first example of an image displayed on a display unit of an HMI (Human machine interface).
Figure 6B:
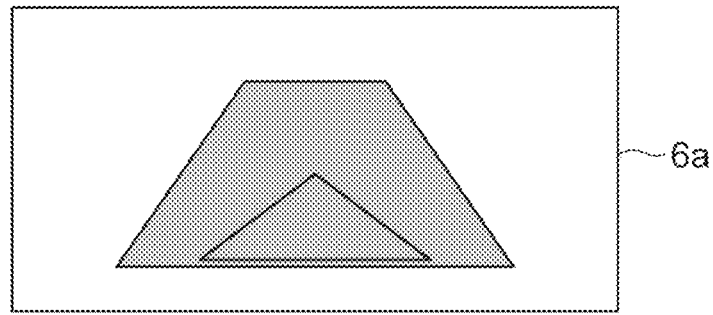
FIG. 6B is a diagram illustrating a second example of an image displayed on the display unit of the HMI.
Figure 6C:
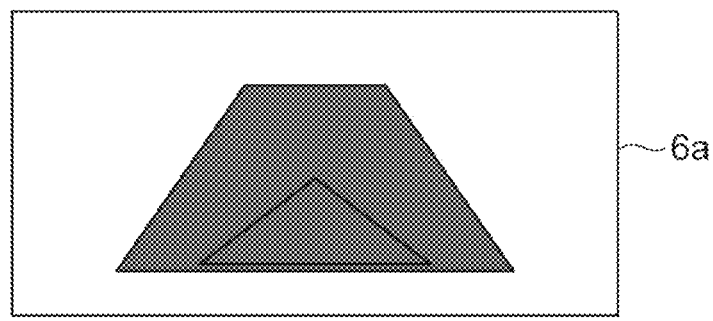
FIG. 6C is a diagram illustrating a third example of an image displayed on the display unit of the HMI.

As illustrated in FIG. 6A, in a state in which both the driving readiness degree and the recommended driving readiness degree are low, both the trapezoidal icon and the triangular icon are displayed in a first color (for example, light blue). As illustrated in FIG. 6B, in a state in which both the driving readiness degree and the recommended driving readiness degree are low, both the trapezoidal icon and the triangular icon are displayed in a second color (yellow, for example) that urges a warning than that of the first color. As illustrated in FIG. 6C, in a state in which both the driving readiness degree and the recommended driving readiness degree are low, both the trapezoidal icon and the triangular icon are displayed in a third color (for example, red) that urges the warning than that of the second color.

Figure 6D:
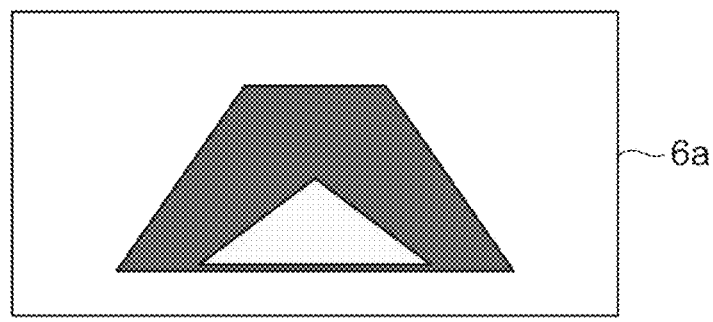
FIG. 6D is a diagram illustrating a fourth example of an image displayed on the display unit of the HMI.

As illustrated in FIG. 6D, in a state in which the driving readiness degree is low and the recommended driving readiness degree is high, those states are displayed on the display unit 6a such that the recommended driving readiness degree becomes equal to or lower than the driving readiness degree. That is, the trapezoidal icon is displayed in the third color, and the triangular icon is displayed in the first color. As a result, the driver concentrates his/her attention on the driving situation such that the driving readiness degree increases. When the host vehicle is in the autonomous driving, the set vehicle speed decreases and the inter-vehicle time increases, and thus, the recommended driving readiness degree decreases. When the host vehicle is in the manual driving, the driver decreases the vehicle speed and lengthens a vehicle-to-vehicle distance such that the recommended driving readiness degree decreases.

If the HMI 6 can give a stimulation to the driver with at least one of vibration and smell, or if the driving readiness degree is low and the recommended driving readiness degree is high, the stimulus may be given such that the recommended driving readiness degree becomes equal to or lower than the driving readiness degree.

As described above, in the driving consciousness estimation device 100, the influence of the reaction time on the driving readiness degree is greater than the influence of the inattention time and the arousal level. As a result, since it can be seen that the reaction time of the driver further contributes to the driving safety than the inattention time and the arousal level of the driver, it is possible to estimate the driving readiness degree with sufficient consideration of the driving safety. It is possible to improve the driving safety.

FIG. 7A is a flowchart illustrating another example of estimation processing performed by the driving readiness degree estimation unit 17. FIG. 7B is a diagram illustrating a third table T3. The driving readiness degree estimation unit 17 may estimate the driving readiness degree with reference to the third table T3 (refer to FIG. 7B) instead of the first table T1 and the second table T2. The third table T3 is set in advance and stored in the storage unit of the ECU 10, for example. The third table T3 is a table when the reaction time is equal to or longer than the reaction threshold value.

For the driving readiness degree in the third table T3, similarly to each table described above, the arousal level is divided into "High" and "Low". For the driving readiness degree in the third table T3, similarly to each table described above, the inattention time is divided into "Long", "Medium" and "Short". In the third table T3, the driving readiness degree when the arousal level is "Low" and the inattention time is "Long" is indicated as "X (N/A)" because the driving readiness degree is extremely low and there is no corresponding degree.

When estimating the driving readiness degree using the third table T3, the driving readiness degree estimation unit 17 may estimate the driving readiness degree as follows. As illustrated in FIG. 7A, first, it is determined whether or not the reaction time is shorter than the reaction threshold value (STEP S21). If YES in STEP S21 described above, the driving readiness degree is estimated as "High" (first degree) (STEP 522). If NO in STEP S21 described above, a degree (a second degree) corresponding to the inattention time and the arousal level is estimated as the driving readiness degree with reference to the third table T3 (STEP S23).

As a result thereof, if the reaction time is shorter than the threshold value (reaction is fast), the driving readiness degree becomes High, and if the reaction time is equal to or longer than the threshold value (the reaction is slow), even if the inattention time and the arousal level change, the driving readiness degree becomes equal to or lower than "Medium Low". When the reaction time changes, the driving readiness degree is changed by equal to or more than two steps. When the inattention time is changed by one step, the driving readiness degree is not changed or is changed by one step. When the arousal level is changed, the driving readiness degree is not changed or is changed by one step. That is, the influence of the reaction time on the driving readiness degree estimated by the driving readiness degree estimation unit 17 is greater than the influence of at least one of the inattention time and the arousal level on the driving readiness degree.

FIG. 8A is a flowchart illustrating still another example of estimation processing performed by the driving readiness degree estimation unit 17. FIG. 8B is a diagram illustrating a fourth table T4. The driving readiness degree estimation unit 17 may estimate the driving readiness degree with reference to the fourth table T4 (refer to FIG. 8B) instead of the first table T1 and the second table T2. The fourth table T4 is set in advance and stored in the storage unit of the ECU 10, for example.

For the driving readiness degree in the fourth table T4, similarly to each table described above, the arousal level is divided into "High" and "Low". For the driving readiness degree in the fourth table T4, similarly to each table described above, the inattention time is divided into "Long", "Medium" and "Short". In the fourth table T4, the driving readiness degree when the arousal level is "Low" and the inattention time is "Long" is indicated as "X (N/A)" because the driving readiness degree is extremely low and there is no corresponding degree.

When estimating the driving readiness degree using the fourth table T4, the driving readiness degree estimation unit 17 may estimate the driving readiness degree as follows. As illustrated in FIG. 8A, first, a preliminary driving readiness degree corresponding to the inattention time and the arousal level is determined with reference to the fourth table T4 (STEP S31). It is determined whether or not the reaction time is shorter than the reaction threshold value (STEP S32). If YES in STEP S32 described above, a degree obtained by increasing the preliminary driving readiness degree by 2 steps is estimated as the driving readiness degree (STEP S33). If NO in STEP S32 described above, the preliminary driving readiness degree is estimated as the driving readiness degree (STEP S34).

As a result thereof, if the reaction time is shorter than the threshold value (reaction is fast), the driving readiness degree is changed by two steps than that when the reaction time is equal to or longer than the threshold value (the reaction is slow). When the inattention time is changed, the driving readiness degree is changed by one step. When the arousal level is changed, the driving readiness degree is changed by one step. That is, the influence of the reaction time on the driving readiness degree estimated by the driving readiness degree estimation unit 17 is greater than the influence of at least one of the inattention time and the arousal level on the driving readiness degree.

In the present embodiment, for example, if the reaction time cannot be recognized by the reaction time recognition unit 14 because the viewing target for determining the reaction time is not present, the driving readiness degree estimation unit 17 may estimate the driving readiness degree based on only the inattention time and the arousal level. For example, if the reaction time cannot be recognized, the driving readiness degree estimation unit 17 may estimate the driving readiness degree referring to a table not dependent on the reaction time (for example, the third table T3 or the like in FIG. 7B).

Second Embodiment

Next, a second embodiment will be described. In the description of the second embodiment, points different from that in the first embodiment will be described, and the redundant description will not be repeated.

As illustrated in FIG. 9, a driving consciousness estimation device 200 according to the second embodiment estimates the driving readiness degree when the driver is driving the host vehicle with manual driving. The driving consciousness estimation device 200 includes a visual field recognition unit 214 instead of the reaction time recognition unit 14 (refer to FIG. 1) as a functional configuration of the ECU 10.

Figure 10:
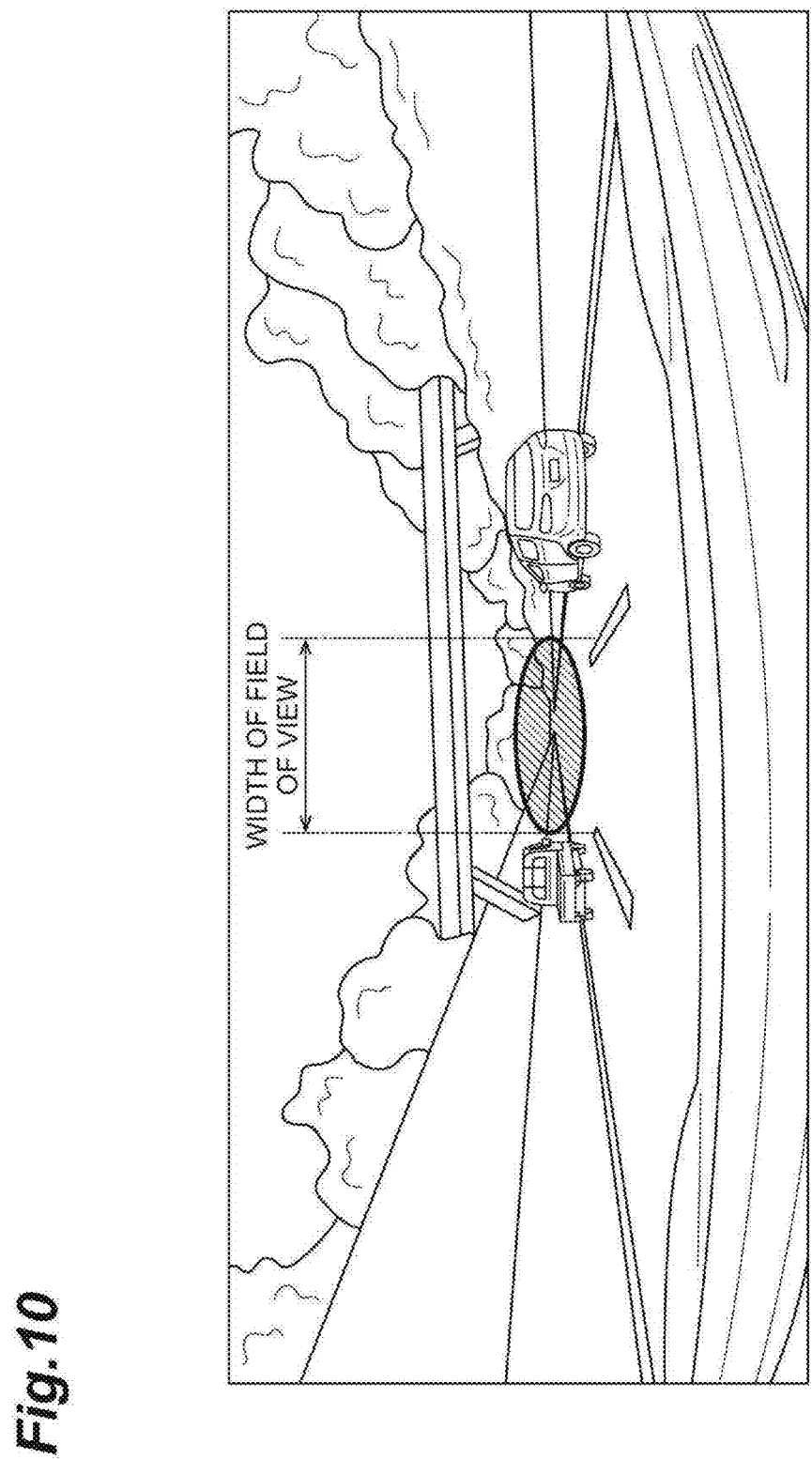
FIG. 10 is a diagram illustrating a width of field of view.

The visual field recognition unit 214 recognizes a width of the field of view of the driver based on, for example, the driver image acquired by the driver image acquisition unit 11. For example, as illustrated in FIG. 10, the visual field recognition unit 214 can obtain the width H of the field of view from the left and right line of sight movement ranges of the driver at a constant vehicle speed (for example, about 100 km/h). The method of recognizing the width H of the field of view is not particularly limited, and various well-known methods can be adopted.

Figure 11:
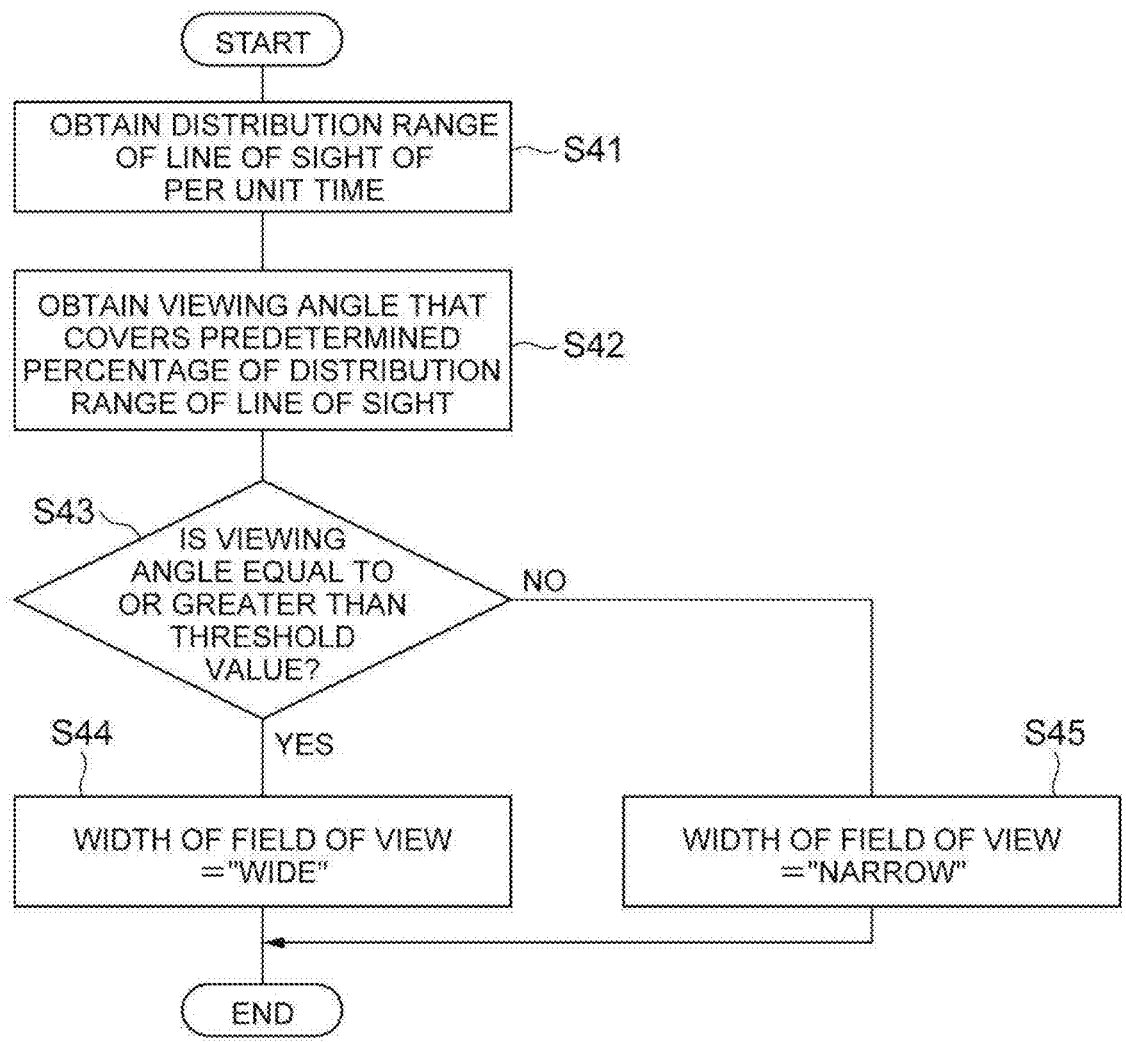
FIG. 11 is a flowchart illustrating processing for recognizing the width of the field of view.

As an example of processing by the visual field recognition unit 214, as illustrated in FIG. 11, first, the distribution range of the line of sight of the driver per unit time is obtained (STEP S41), and then, a viewing angle that covers the predetermined percentage of the distribution range of the line of sight is obtained (STEP S42). The prescribed percentage is not 100% but 70% to 90%, in order to eliminate the influence of a short time inattention being included. It is determined whether or not the viewing angle obtained in STEP S42 is equal to or greater than a set angle (STEP S43). The set angle is determined in advance and stored in the storage unit of the ECU 10, for example. The set angle is, for example, an angle of 7 degrees or near to 7 degrees. If YES in STEP S43 described above, the width of the field of view is recognized as "Wide" (STEP S44). If NO in STEP S43 described above, the width of the field of view is recognized as "Narrow" (STEP S45).

If the driver is driving the host vehicle with manual driving, the driving readiness degree estimation unit 17 in the present embodiment estimates the driving readiness degree based on the width of the field of view recognized by the visual field recognition unit 214, the inattention time recognized by the inattention time recognition unit 15, and the arousal level recognized by the arousal level recognition unit 16.

The driving readiness degree estimation unit 17 estimates the driving readiness degree with reference to a fifth table T5 (refer to FIG. 12A) and a sixth table T6 (refer to FIG. 12B). The fifth table T5 is a table when the width of the field of view is wide. The sixth table T6 is a table when the width of the field of view is narrow. The fifth table T5 and the sixth table T6 are set in advance and are stored in the storage unit of the ECU 10, for example.

For the driving readiness degree in the fifth table T5 and sixth table T6, similarly to each table described above, the arousal level is divided into "High" and "Low". For the driving readiness degree in the fifth table T5 and sixth table T6, similarly to each table described above, the inattention time is divided into "Long", "Medium" and "Short". In the sixth table T6, the driving readiness degree when the arousal level is "Low" and the inattention time is "Long" is indicated as "X (N/A)" because the driving readiness degree is extremely low and there is no corresponding degree.

The arousal level recognized by the arousal level recognition unit 16, the inattention time recognized by the inattention time recognition unit 15, and the width of the field of view recognized by the visual field recognition unit 214 are input to the driving readiness degree estimation unit 17. When the width of the field of view is wide, the driving readiness degree estimation unit 17 estimates the first degree corresponding to the inattention time and the arousal level as the driving readiness degree with reference to the fifth table T5. When the width of the field of view is narrow, the driving readiness degree estimation unit 17 estimates the second degree corresponding to the inattention time and the arousal level as the driving readiness degree with reference to the sixth table T6.

As indicated in the fifth table T5 and the sixth table T6, even if the inattention time and the arousal level are changed, the driving readiness degree becomes equal to or higher than "Medium" if the width of the field of view is wide, and the driving readiness degree becomes lower than "Medium" if the width of the field of view is narrow. When the inattention time is changed by one step, the driving readiness degree is not changed or is changed by one step. When the arousal level is changed, the driving readiness degree is not changed or is changed by one step. On the other hand, when the width of the field of view is changed (compare the fifth table T5 with the sixth table T6), the driving readiness degree is changed by equal to or more than two steps. The influence of the width of the field of view on the driving readiness degree estimated by the driving readiness degree estimation unit 17 is greater than the influence of at least one of the inattention time and the arousal level on the driving readiness degree.

As described above, in the driving consciousness estimation device 200, if the driver is driving the host vehicle with the manual driving, the driving readiness degree estimation unit 17 estimates the driving readiness degree based on the width of the field of view and at least one of the inattention time and the arousal level. The influence of the width of the field of view on the driving readiness degree is greater than the influence of the inattention time and the arousal level. As a result, since it can be seen that the width of the field of view of the driver further contributes to the driving safety than the inattention time and the arousal level of the driver, it is possible to estimate the driving readiness degree with sufficient consideration of the driving safety. It is possible to improve the driving safety. Especially, at the time of manual driving in which it is difficult to appropriately determine the reaction of the driver, it is possible to appropriately estimate the driving readiness degree based on the width of the field of view of the driver.

Third Embodiment

Next, a third embodiment will be described. In the description of the third embodiment, points different from that in the first embodiment will be described, and the redundant description will not be repeated.

Figure 13:
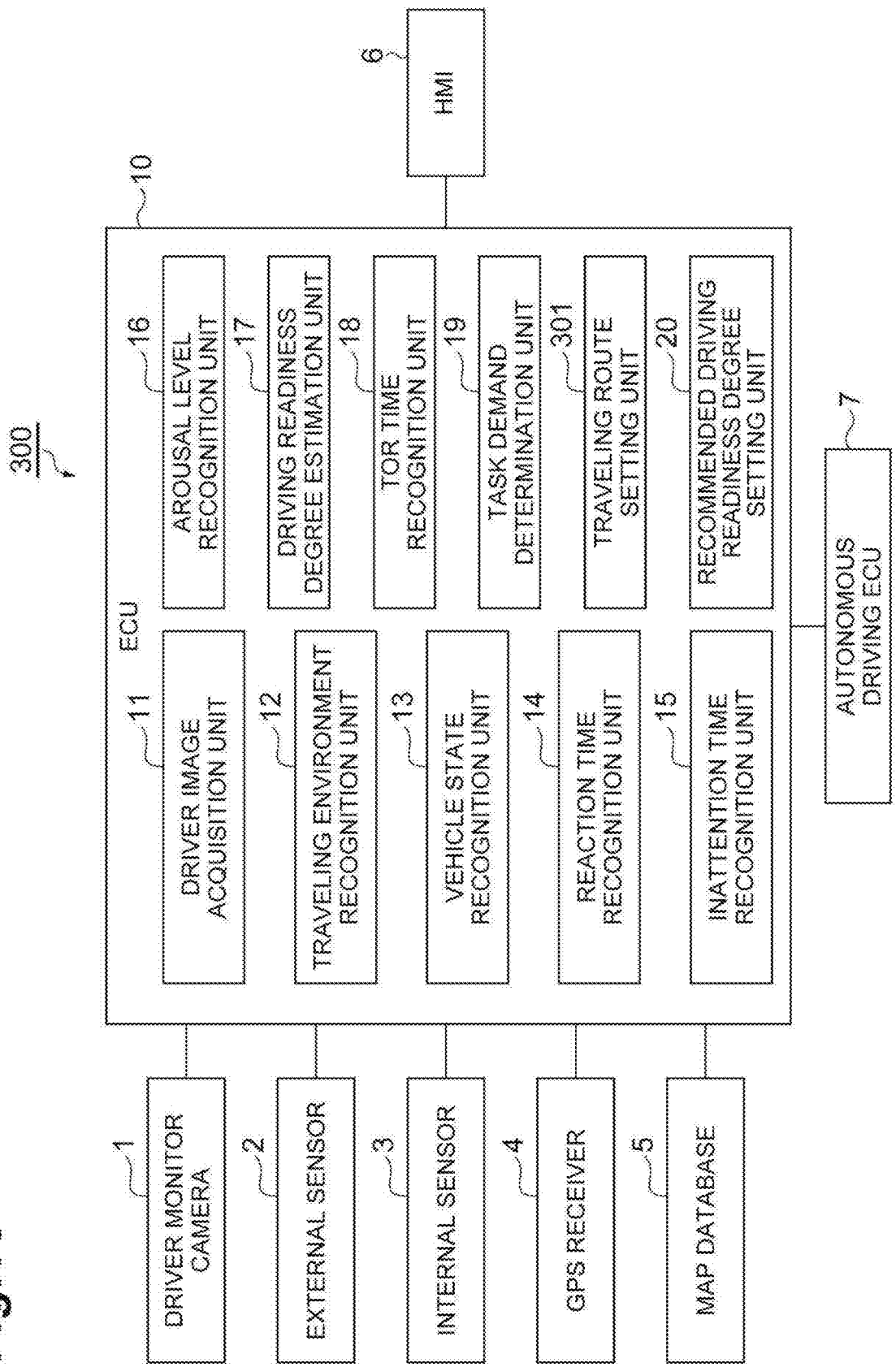
FIG. 13 is a block diagram illustrating a driving consciousness estimation device according to a third embodiment.

As illustrated in FIG. 13, a driving consciousness estimation device 300 according to the third embodiment further includes a traveling route setting unit 301 as a functional configuration of the ECU 10. The traveling route setting unit 301 sets a traveling route for which the host vehicle is scheduled to travel, based on, for example, an operation input from an occupant of the host vehicle or a target route input from a well-known navigation system.

Figure 14:
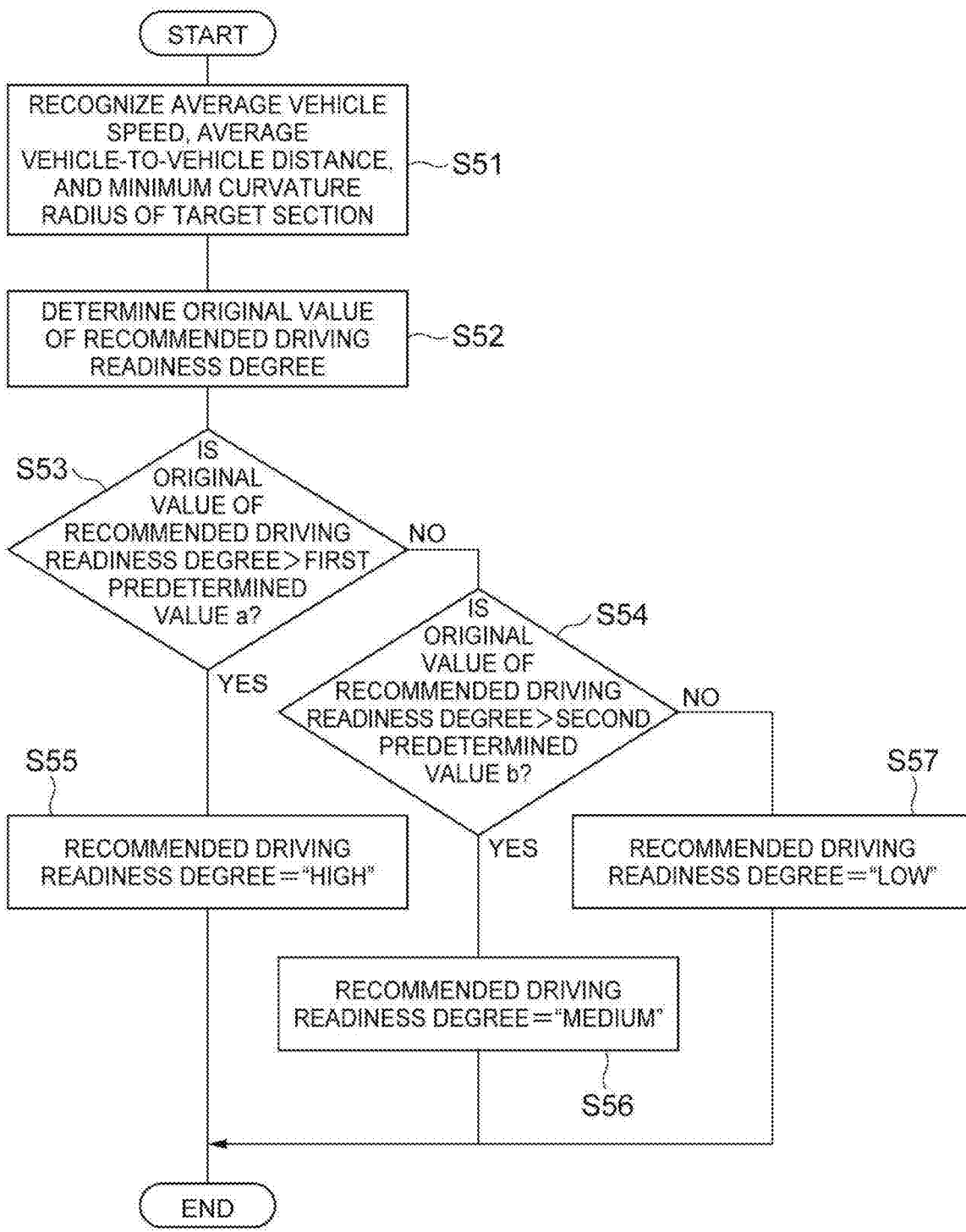
FIG. 14 is a flowchart illustrating processing for setting the recommended driving readiness degree.

The recommended driving readiness degree setting unit 20 in the present embodiment sets the recommended driving readiness degree recommended for the traveling route set by the traveling route setting unit 301. Specifically, the recommended driving readiness degree setting unit 20 sets the recommended driving readiness degree in each target section formed by dividing the traveling route as follows. As illustrated in FIG. 14, first, an average vehicle speed, an average vehicle-to-vehicle distance, and a minimum curvature radius of the target section are recognized (STEP S51). For example, the average vehicle speed, the average vehicle-to-vehicle distance, and the minimum curvature radius can be recognized from the road information from the navigation system or the like. The method of recognizing the average vehicle speed, the average vehicle-to-vehicle distance, and the minimum curvature radius is not particularly limited, and various well-known methods can be adopted.

According to the following mathematical expression, the original value of the recommended driving readiness degree is determined (STEP S52). Original value of recommended driving readiness degree=α×(average vehicle speed/minimum curvature radius)×(1/average vehicle-to-vehicle distance).

It is determined whether or not the original value of the recommended driving readiness degree is higher than a first predetermined value a (STEP S53). If NO in STEP S53, it is determined whether or not the original value of the recommended driving readiness degree is higher than a second predetermined value b (STEP S54). Here, the first predetermined value a>the second predetermined value b. If YES in STEP S53, the recommended driving readiness degree is set as "High" (STEP S55). If YES in STEP S54, the recommended driving readiness degree is set as "Medium" (STEP S56). If NO in STEP S54, the recommended driving readiness degree is set as "Low" (STEP S57).

Figure 15:
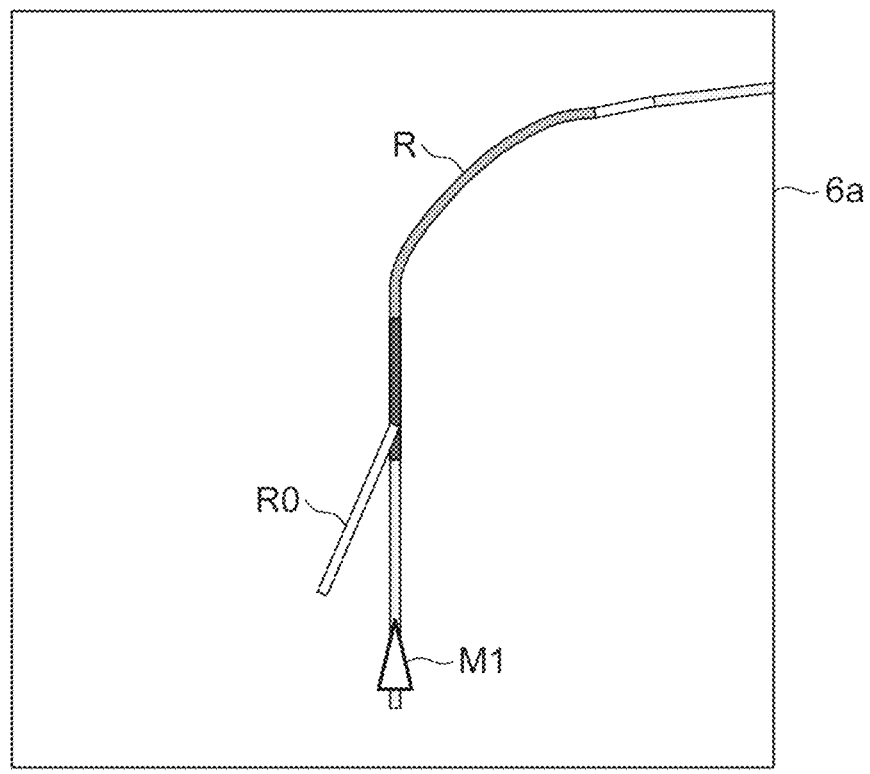
FIG. 15 is a diagram illustrating an example of an image displayed on the display unit of the HMI.

FIG. 15 is a diagram illustrating an example of an image displayed on the display unit 6a of the HMI 6 in the driving consciousness estimation device 300. A triangular icon on the display unit 6a is a host vehicle mark M1 indicating a state of the driving readiness degree estimated by the driving readiness degree estimation unit 17. The host vehicle mark M1 is displayed in a color corresponding to the state of the driving readiness degree. For example, if the driving readiness degree is "High", the host vehicle mark M1 is displayed in red. If the driving readiness degree is "Medium", the host vehicle mark M1 is displayed in orange color. If the driving readiness degree is "Low", the host vehicle mark M1 is displayed in green. The host vehicle mark M1 may indicate the driving readiness degree in magnitude instead of or in addition to the color.

The line on the display unit 6a represents the traveling route R and another route RO other than the traveling route. In the traveling route R, each target section is color coded according to the recommended driving readiness degree. For example, if the recommended driving readiness degree is "High", the traveling route R is displayed in red. If the recommended driving readiness degree is "Medium", the traveling route R is displayed in orange color. If the recommended driving readiness degree is "Low", the traveling route R is displayed in green. The traveling route R may indicate the recommended driving readiness degree in magnitude instead of or in addition to the color. Another route RO does not display information on a recommended driving readiness degree (in this case, a specific color).

According to the display illustrated in FIG. 15, the future recommended driving readiness degree can be easily understood. If there is a gap between the future and current driving readiness degrees, the driver can widen the vehicle-to-vehicle distance set in advance, or the like such that the future recommended driving readiness degree decreases or such that the current recommended driving readiness degree matches the future driving readiness degree. The driver can increase concentration of the driver by him/herself, and then, can increase the driving readiness degree such that the current recommended driving readiness degree matches the future driving readiness degree.

As described above, the embodiments were described above, an aspect of the present disclosure is not limited to the above-described embodiments. An aspect of the present disclosure can be implemented in various forms including various modifications and improvements based on the knowledge of those skilled in the art, including the above-described embodiments.

The driving consciousness estimation device 200 in the second embodiment and the driving consciousness estimation device 300 in the third embodiment may be combined. In the embodiments described above, it is not always necessary to be connected to the autonomous drive ECU 7, and it is not necessary to configure a part of the autonomous driving system. An aspect of the present disclosure can also be applied to the vehicles that do not perform autonomous driving.

In the embodiments described above, the driving readiness degree is estimated using the tables set in advance, but the driving readiness degree may be estimated using calculation formula set in advance. In the embodiments described above, the driving readiness degree is estimated based on both inattention time and the arousal level of the driver, but the driving readiness degree may be estimated based on at least one of the inattention time and the arousal level. The arousal level may be an index including at least one of the steering wheel grip pressure of the driver, the armrest pressing force, heart rate, electromyogram information and electroencephalogram pattern.

What is claimed is:

1. A driving consciousness estimation device comprising:
an electronic control unit (ECU) programmed to:
estimate a driving readiness degree relating to a driving consciousness of a driver based on: (i) a reaction time or a width of field of view of the driver of a vehicle, and (ii) both a time duration of an eye glance away from a road environment and an arousal level of the driver,
wherein an influence of the reaction time or the width of the field of view on the estimated driving readiness degree is greater than an influence of the time duration of eye glance away from road environment and the arousal level on the driving readiness degree,
determine a recommended driving readiness degree based on (i) a time required for switching a driving mode of the vehicle from autonomous driving to manual driving and (ii) a task demand required of the driver after the driving mode is switched from the autonomous driving to the manual driving, and
display, on a display unit, a state of both the estimated driving readiness degree and the recommended driving readiness degree for the driver.

2. The driving consciousness estimation device according to claim 1,
wherein, the ECU is further programmed to estimate the driving readiness degree based on (i) the width of the field of view and not the reaction time, and (ii) time duration of the eye glance away from road environment and the arousal level, if the driver is driving the vehicle with manual driving.

3. The driving consciousness estimation device according to claim 1,
wherein, the ECU is further programmed to estimate the driving readiness degree based on only the time duration of the eye glance away from the road environment and the arousal level, if the reaction time cannot be recognized.

4. The driving consciousness estimation device according to claim 1,
wherein, the ECU is a part of an autonomous driving system.

5. The driving consciousness estimation device according to claim 1, wherein, the ECU is further programmed to:

determine whether the reaction time is shorter than a reaction threshold value, and
based upon the determination that the reaction time is shorter than the reaction threshold value, estimate the driver readiness degree as medium, medium high or high,
based upon the determination that the reaction time is not shorter than the reaction threshold value, estimate the driver readiness degree as low or medium low,
wherein the driver readiness degree increases in steps in the recited order of: low, medium low, medium, medium high and high.

6. The driving consciousness estimation device according to claim 1, wherein, the ECU is further programmed to:
determine whether the reaction time is shorter than a predetermined time,
determine whether or not a task demand is high based on a traveling environment of the vehicle and a state of the vehicle, wherein the task demand is high if (a) a follow up traveling against a preceding vehicle and a preceding inter-vehicle time is at least 1.0 second, and (b) the vehicle is traveling on a curve and a lateral acceleration of the vehicle is less than 2 m/s$^2$, and
set the recommended driving readiness degree as high if (1) the reaction time is shorter than the predetermined time and (2) the task demand is high,
set the recommended driving readiness degree as medium if (1) the reaction time is shorter than the predetermined time and (2) the task demand is not high,
set the recommended driving readiness degree as medium if (1) the reaction time is not shorter than the predetermined time and (2) the task demand is high, and
set the recommended driving readiness degree as low if (1) the reaction time is not shorter than the predetermined time and (2) the task demand is not high,
wherein the recommended readiness degree increases in steps in the recited order of: low, medium and high.

7. The driving consciousness estimation device according to claim 1, wherein, the ECU is further programmed to:
wherein the arousal level is categorized as low or high, and the time duration of the eye glance away from the road environment is categorized as long, medium or short,
determine whether the reaction time is shorter than a threshold value,
based upon a determination that the reaction time is shorter than the threshold value, estimate the driving readiness degree as high,
based upon a determination that the reaction time is not shorter than the threshold value, estimate the driving readiness degree based on (1) the arousal level and (2) the time duration of the eye glance away from the road environment:
wherein, estimate the driving readiness degree is low when (1) the arousal level is low and (2) the time duration of the eye glance away from the road environment is medium or short,
estimate the driving readiness degree is medium low when (1) the arousal level is high and (2) the time duration of the eye glance away from the road environment is short.

8. The driving consciousness estimation device according to claim 1, wherein, the ECU is further programmed to:
determine a preliminary driving readiness degree corresponding to the arousal level and the time duration of the eye glance away from the road environment, before the reaction time can be determined.

9. The driving consciousness estimation device according to claim 1, wherein the display shows the state of each of the estimated driving readiness degree and the recommended driving readiness degree as respective icons that are overlapped with each other on the display.

\* \* \* \* \*